US005333605A

United States Patent [19]

Matsumura et al.

[11] Patent Number: 5,333,605

[45] Date of Patent: Aug. 2, 1994

[54] REMEDIAL DEVICE FOR HAND INSUFFICIENCY

[75] Inventors: Mitsuma Matsumura, Tokyo; Kenji Mizuno, Sakado; Atsuki Hashimoto, Tokyo, all of Japan

[73] Assignee: Nitto Kohki Co., Ltd., Tokyo, Japan

[21] Appl. No.: 19,236

[22] Filed: Feb. 18, 1993

[30] Foreign Application Priority Data

May 11, 1992 [JP] Japan ................................ 4-037967
May 11, 1992 [JP] Japan ................................ 4-144845

[51] Int. Cl.[5] ................................................ A61F 5/00

[52] U.S. Cl. ........................................ 601/40; 602/21; 602/22

[58] Field of Search ......................... 128/26, DIG. 20; 602/21, 22; 482/44, 47, 49

[56] References Cited

U.S. PATENT DOCUMENTS

| | | |
|---|---|---|
| 2,438,144 | 3/1948 | Bunyar, Jr. . |
| 2,553,277 | 5/1951 | Robinson et al. . |
| 2,880,721 | 4/1959 | Corcoran . |
| 3,457,912 | 7/1969 | Clark et al. . |
| 3,581,740 | 6/1971 | Sherbourne . |
| 3,937,215 | 2/1976 | Barthlome . |
| 4,173,218 | 11/1979 | Cronin . |
| 4,274,399 | 6/1981 | Mummert . |
| 4,522,197 | 6/1985 | Hasegawa . |
| 4,596,240 | 6/1986 | Takahasi et al. . |
| 4,619,250 | 10/1986 | Hasegawa . |
| 4,671,258 | 6/1987 | Barthlome . |
| 4,706,658 | 11/1987 | Cronin . |
| 4,807,606 | 2/1989 | Hasegawa et al. . |

FOREIGN PATENT DOCUMENTS

| | | |
|---|---|---|
| 735700 | 5/1963 | Canada . |
| 73434 | 4/1893 | Fed. Rep. of Germany . |
| 486522 | 4/1916 | France . |
| 2-15471 | 2/1990 | Japan . |
| 2008953 | 6/1978 | United Kingdom . |
| 2126110 | 3/1984 | United Kingdom . |
| 2147812 | 5/1985 | United Kingdom . |

*Primary Examiner*—Richard J. Apley
*Assistant Examiner*—Lynne Reichard
*Attorney, Agent, or Firm*—Wenderoth, Lind & Ponack

[57] ABSTRACT

A remedial device for hand insufficiency includes a glove trank having a foundation and allowing the palm of a hand to be applied thereto, the thumb and fingers of the hand to be fixed to the foundation with finger stoppers, and the wrist and forearm to be fixed to the foundation with an arm stopper; a plurality of first bag bodies accommodating finger-spreading air sacks and disposed on the front side of the foundation; a pair of second bag bodies accommodating joint-extending air sacks and disposed on the back side of the foundation; and a compressed air feed and discharge device for inflating and deflating the air sacks in the first and second bag bodies to effect a spreading of the fingers and an extension and dorsiflexion of hand joints. Each of the second bag bodies includes two bag pieces which are each formed of cloth cut into a foundation. The second bag bodies each have a concavity where the foundation is folded about itself and the bag pieces are adjoined to each other through the fold forming the concavity. The arm stopper includes a wrist strap extending laterally from one side of the foundation and having a length sufficient to be wound around the wrist at least one and a half times and a pair of forearm straps.

11 Claims, 7 Drawing Sheets

REMEDIAL DEVICE FOR HAND INSUFFICIENCY

BACKGROUND OF THE INVENTION

1. Field of the Invention

This invention relates to a remedial device for hand insufficiency, which aids in restoring normal functions of arm joints, hands and fingers by overcoming hindrances inflicted thereon in consequence of diseases and lesions of the central nervous system such as cerebrovascular lesions, epicerebral injuries, cerebral palsy and spinal lesions, injuries of the peripheral nerves, and injuries of the joints and muscles. More particularly, this invention relates to bag bodies for accommodating air sacks which allow fingers to be expanded and hand joints to be extended and dorsiflexed.

2. Description of the Prior Art

When the aforementioned various diseases and lesions have inflicted functional disorders on forearms, arm joints, hands, and fingers, it becomes necessary to cure these diseases and lesions and, at the same time, strive for restoration of motility through training. It has long been held that the restoration of the function of the arm joints, hands and fingers is extremely difficult. In spite of a myriad of studies being performed recently in the medical science of rehabilitation, a satisfactory remedial device has not yet been developed. An attempt at enabling arm joints, hands and fingers handicapped in the function of flexion, contracture or extension to be extended by the action of air pressure or a spring results in the production of complicated motions which more often than not impose uncalled-for burdens on patients. The conventional devices which are based on this operating principle have produced no satisfactory results.

For example, U.S. Pat. No. 4,807,606 discloses such a remedial device which comprises a glove body (trank) of palm cloth resembling a hand having the four fingers and thumb thereof spread out, finger stoppers disposed on the front side of the trank and adapted to individually fix the thumb and fingers in their spread state, a hand back stopper for fixing the back of the hand, a wrist stopper and an arm stopper jointly adapted to fix the trank to the arm, first bag bodies interposed between the fingers and adapted to accommodate air sacks causing the fingers to be spread out, second bag bodies disposed on the back side of the trank and accommodating therein air sacks extended from the palm to the inner arm surface of the arm and used to cause extension of joints, and air tubes connecting the air sacks to a compressed air feed and discharge device.

By repeating the cycle of feeding compressed air to the air sacks and, after a required duration, discharging the air from the air sacks, the prior art device enables the hand joints and fingers in the state of dysfunction, respectively, to produce motions of extension and dorsiflexion and a motion of expansion rhythmically and intermittently and, as a result, relieves patients of dysfunctions in flexion, contracture and extension and, at the same time, gives rise in the patients to a factor for inducing autokinesis.

The prior art device is capable of manifesting a curative effect not attained to date and commands high esteem currently in the therapeutic field. It nevertheless has a problem in the following points.

In the prior art device, the trank has a total of eight bag bodies on the front and back sides thereof each for accommodating an air sack. With respect to the front side of the trank, since the bag bodies for the air sacks to be individually used between the index finger and the middle finger, between the middle finger and the ring finger and between the ring finger and little finger are usable on a trank for either hand and the bag body for accommodating the air sack to be used between the thumb and the index finger is different on the tranks for both hands, glove foundations can be obtained from just two kinds of patterns. As far as the front side of the trank is concerned, the manufacture of the device under discussion including the work of sewing bag bodies entails no particular problem regarding manufacturing time and product quality.

As illustrated in FIG. 9, however, a trank 80 is provided on the back side 81 of a glove foundation with bag bodies 82, 83, 84 and 85 differing in shape from one another and serving to accommodate air sacks similarly to the bag bodies on the front side. These four bag bodies 82 to 85 are formed by cutting foundations for differently shaped bag bodies from one sheet of cloth, respectively, using four patterns, attaching slide fasteners 82*a*, 83*a*, 83*b*, 84*a*, 85*a* and 85*b* to relevant positions on the foundations, and binding gussets (not shown). The device is then finished by sewing the bag bodies 82 to 85 to the back side 81 of the glove foundation and sewing the adjoining parts of the bag bodies 82 to 85 together.

Various disadvantages arise where the plural kinds of bag bodies are large as in the case of FIG. 9. For example, the work of cutting the foundations for bag bodies from the cloth takes much time and the work of sewing the bag bodies consumes much time. Further, since the bag bodies are separated from one another, the work of sewing them to the glove foundation consumes much time and tends to result in discrepancies in the quality of workmanship. It is held that the bag bodies 83 and 85 particularly prohibit uniformization in the work of sewing because they are large and, moreover, are disposed over a wide range from the entire palm over the inner surface of the forearm and are possessed of a dart 86 which determines the condition of dorsiflexion in the motion of extension. When the workmanship of sewing varies between the bag bodies 83 and 85, this variation imparts twists to these bag bodies and causes a change in size and compels the dart 86 to give rise to a difference in angle of dorsiflexion or in position of dorsiflexion between the two bag bodies. In other words, deformation of the trank 80 constitutes itself an obstacle to the manifestation of a higher curative effect. The device, therefore, has a problem as to how the product quality (in terms of shape and dorsiflexion) should be uniformized.

Further, in the prior art device, the emplacement of a hand on the palm cloth is attained by fixing the fingers of the hand to the palm cloth with the finger stoppers formed in the relevant positions thereon and fastening the wrist and forearm to the palm cloth by winding the arm stoppers (the wrist stopper and the hand arm stopper), extending laterally in the opposite directions from the opposite sides of the palm cloth at the wrist position and the forearm position, around the wrist and the forearm in such a manner as to intersect each other, and then joining VELCRO fasteners provided on the arm stoppers. The fixation of the back of the hand to the palm cloth is attained by securing one hand back stopper provided near where the bases of the thumb and index finger would lie on the palm cloth to the wrist stopper with VELCRO fasteners.

However, when it is attempted to emplace a hand whose fingers are handicapped with contracture on the palm cloth in the manner described above, since only the hand back stopper is used in fixing the back of the hand, the possibility arises that the little finger side of the hand will float up from the palm cloth. The arm stoppers are adapted to be opened in the manner of a double door and, therefore, have the possibility of producing weak fixing power. When the wrist stopper is not fixed steadily, the possibility exists that the wrist will not fit the palm cloth and will produce an empty space thereunder. Owing to these disadvantages, there have rarely been times when the motion of expanding the little finger side of the hand and the motion of extension for dorsiflexing the wrist joint toward the back of the hand are not produced sufficiently during the feeding of the compressed air to the air sacks.

SUMMARY OF THE INVENTION

The present invention has been produced for the purpose of solving the problems mentioned above.

An object of this invention is to provide a product of high practical utility by decreasing the number of kinds of bag bodies for accommodating air sacks, curtailing the component steps of the manufacturing process thereof ranging from the work of cutting to that of sewing, and uniformizing the product quality.

Another object of this invention is to provide a palm cloth which enables a hand to be fit securely thereto and, consequently, improves the hand's capacity for dorsiflexion in the motion of expansion and the motion of extension more than has been attainable to date, allows induction of autokinesis more effectively, and exhibits an enhanced practical utility.

To attain the above objects, according to this invention there is provided a remedial device for hand insufficiency, comprising a glove trank having a foundation and allowing the palm of a hand to be applied thereto, the thumb and fingers of the hand to be fixed thereto with finger stoppers and the wrist of the hand to be fixed thereto with an arm stopper, a plurality of first bag bodies accommodating finger-spreading air sacks therein and disposed on a front side of the foundation, a pair of second bag bodies accommodating joint-extending air sacks therein and disposed on a back side of the foundation, and a compressed air feed and discharge system for inflating and contracting the air sacks in the first and second bag bodies to effect a spreading of the fingers and extension and dorsiflexion of hand joints, each of the second bag bodies comprising two bag pieces which are each formed of a one-piece cloth foundation of a prescribed shape having a concavity at which the foundation is folded about itself and which pieces are adjoined to each other via the concavity.

One of the second bag bodies having the two bag pieces is formed of a foundation cut from one pattern. The other second bag body may be formed using the foundation inverted. Alternatively, one of the second bag bodies is formed of a foundation cut from a pattern paper and the other second bag body may be cut from the same but inverted pattern.

The two bag pieces of each of the second bag bodies comprise a rectangular portion of a large length and a triangular portion of a small height. The rectangular bag piece is provided in the substantially central part thereof with a dart and, therefore, is endowed with a profile nearly resembling the letter V in an inverted spread state.

The second bag bodies are sewn in a mutually adjoining manner on the back side of the foundation of the trank, and the air sacks accommodated therein are disposed over a wide range including the entire palm and extending to the inner surface of the forearm. Owing to the darts formed in the bag pieces of the larger length (the rectangular portions), the trank will assume a naturally dorsiflexed shape.

The present invention further provides a remedial device for hand insufficiency, comprising a glove trank having a foundation and allowing the palm of a hand to be applied thereto, the thumb and fingers of the hand to be fixed thereto with finger stoppers and the wrist of the hand to be fixed thereto with an arm stopper, a plurality of first bag bodies accommodating finger-spreading air sacks therein and disposed on a front side of the foundation, a pair of second bag bodies accommodating joint-extending air sacks therein and disposed on a back side of the foundation, and a compressed air feed and discharge system for inflating and contracting the air sacks in the first and second bag bodies to effect a spreading of the fingers and the extension and dorsiflexion of hand joints, the arm stopper including a wrist strap extending laterally from one side of the trank and capable of being wound around the wrist at least one and a half times and a pair of forearm straps to secure the forearm to the trank.

In this device, at least two hand back straps extend from the neighborhood where the bases of the thumb and index finger would lie and can be placed tightly over the back of the hand in an intersecting pattern. The free ends of the wrist strap, forearm straps and hand back straps are secured in place through VELCRO fasteners.

When the palm of a hand is placed on the trank, the fingers of the hand are fixed on the trank with the finger stoppers. The forearm of the hand is fixed in place by means of the VELCRO fastener provided on the forearm straps. The fixation of the wrist of the hand is attained by winding the wrist strap around the wrist at least one and a half times and securing the wrist strap in place on the trank by means of the VELCRO fastener provided on the wrist strap.

Then, part of the back of the hand is pressed against the trank by joining one of the hand back straps provided with the VELCRO fastener fast to the wrist strap. The fixation of the finger joints handicapped with contracture is attained by securing the other hand back stopper strap to part of the trank and consequently exerting pressure on the finger joints.

After the remedial device has been prepared for use in the therapy of a hand in a dysfunctional state, desired rehabilitation of the hand is accomplished by feeding compressed air into the air sacks, thereby inflating the air sacks and, as a result, causing the fingers of the hand to be spread and the finger joints to be extended and dorsiflexed. The wrist is tightly pressed against the trank by means of the wrist strap which has been wound around the wrist at least one and a half times and, at the same time, the whole back of the hand is fixed to the trank with one of the hand back straps and the palm is tightly pressed against the trank. Further, by virtue of the other hand back strap, the force of the air sacks is made to act on the joints in the state of contracture. All of these elements cooperate in causing the fingers to be spreading and the joints to undergo a motion of extension with enhanced thoroughness.

The present invention will be better understood and further objects and features thereof will become more apparent when consideration is given to the following detailed description thereof which makes reference to the accompanying drawings.

DETAILED DESCRIPTION OF THE PREFERRED EMBODIMENT

Figure 1:
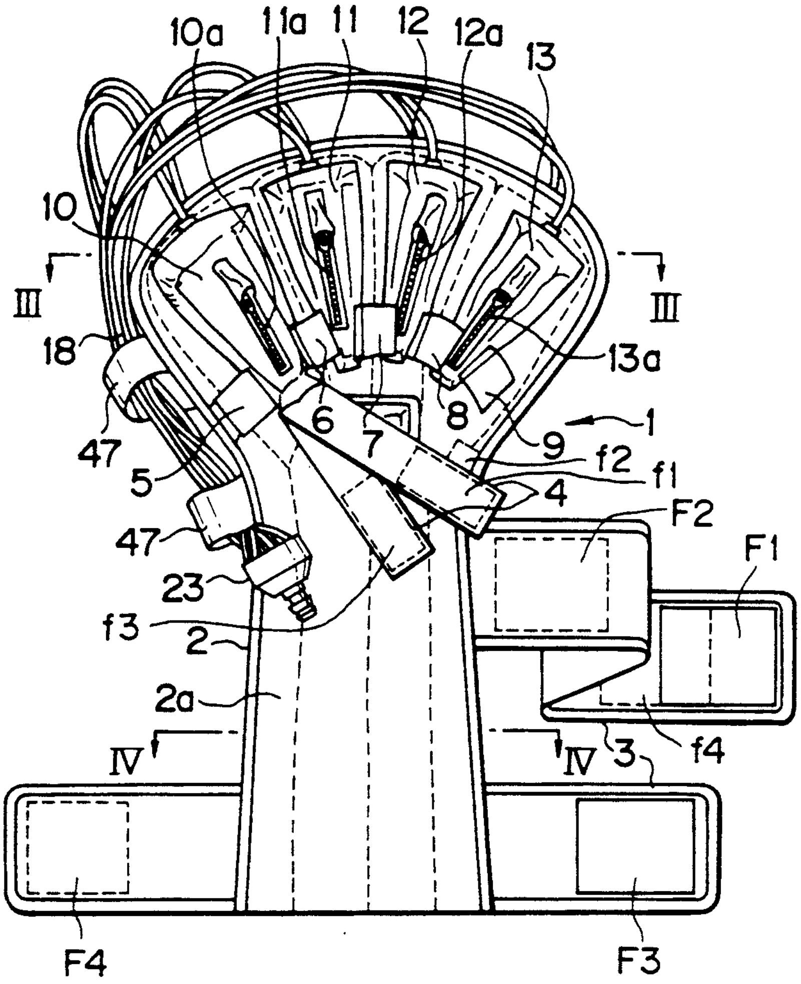
FIG. 1 is a front view of one embodiment of a remedial device for the hand according to the present invention.

This invention will now be described below with reference to one embodiment shown in the accompanying drawings. The drawings represent the remedial device for hand insufficiency in the form of a glove trank to be worn on the right hand. The trank to be worn on the left hand is formed symmetrically with respect to the trank for the right hand and has the same operation and effect as the trank for the right hand and, therefore, will be omitted from the following description.

As illustrated in FIGS. 1 to 4, a trank (glove body) 1 is provided on the front side 2*a* of a glove foundation (palm cloth) 2 with finger stoppers 5, 6, 7, 8 and 9 for fixing fingers, the finger stopper 5 corresponding to the thumb, the finger stopper 6 to the index finger, the finger stopper 7 to the middle finger, the finger stopper 8 to the ring finger, and the finger stopper 9 to the little finger. Bag bodies 10, 11, 12, and 13 provided, respectively, with slide fasteners 10*a*, 11*a*, 12*a* and 13*a* are disposed between where the thumb and fingers are to be placed on the front side 2*a* of the glove foundation 2. Air sacks 10*b*, 11*b*, 12*b* and 13*b* for allowing extension of the fingers are accommodated inside these bag bodies 10 to 13.

A bag body A provided with slide fasteners 19 and 20 and a bag body B which is symmetrical with respect to the bag body A are disposed on the back side 2*b* of the glove foundation 2.

Figure 2:
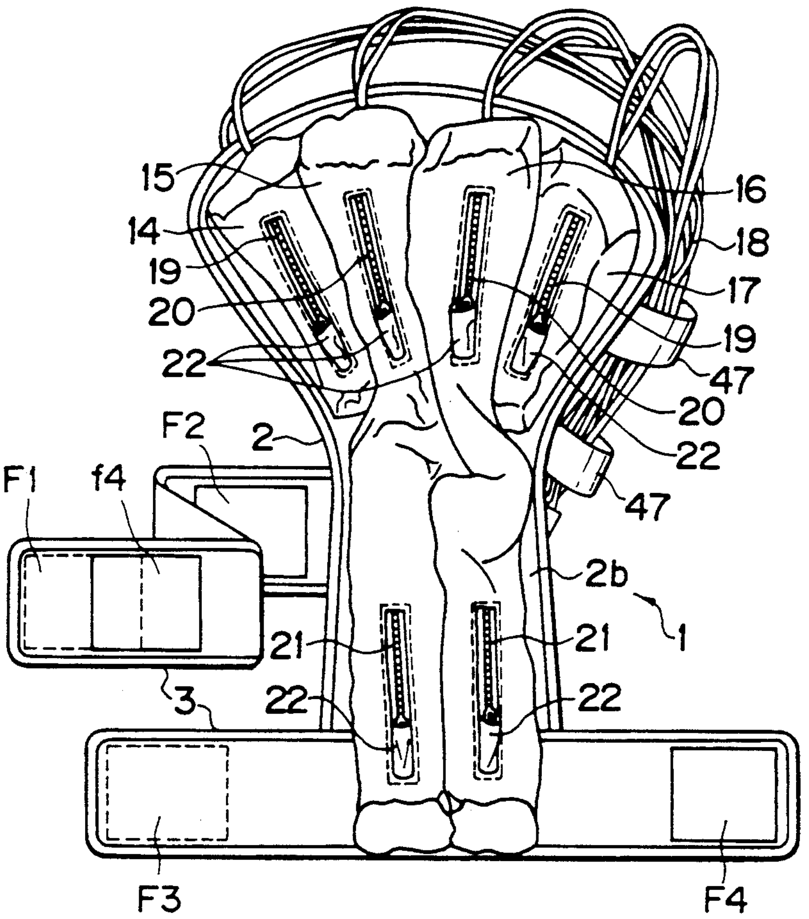
FIG. 2 is a rear view of the device.
Figure 3:
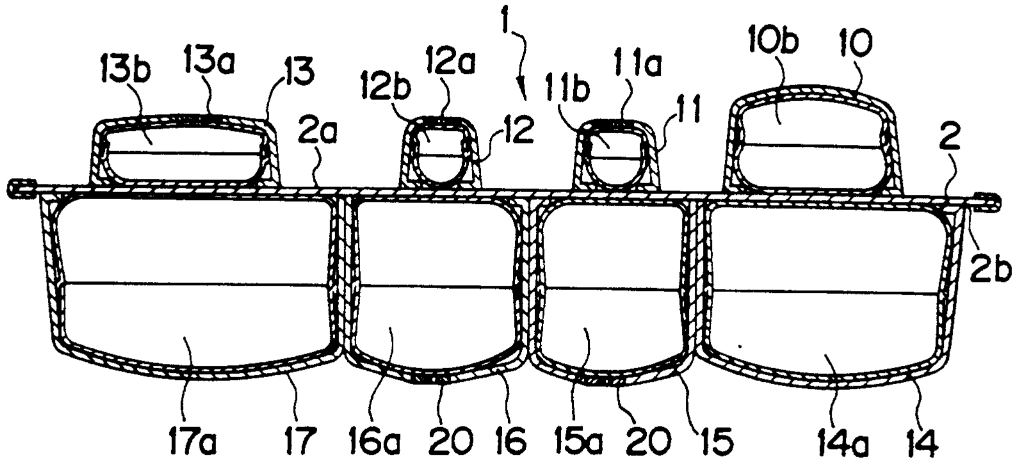
FIG. 3 is a cross-sectional view taken along line III—III in FIG. 1.
Figure 4:
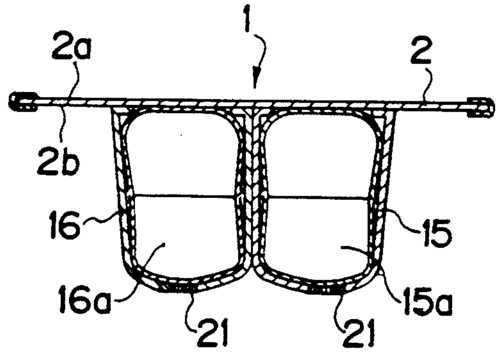
FIG. 4 is a cross-sectional view taken along line IV—IV in FIG. 1.
Figure 6:
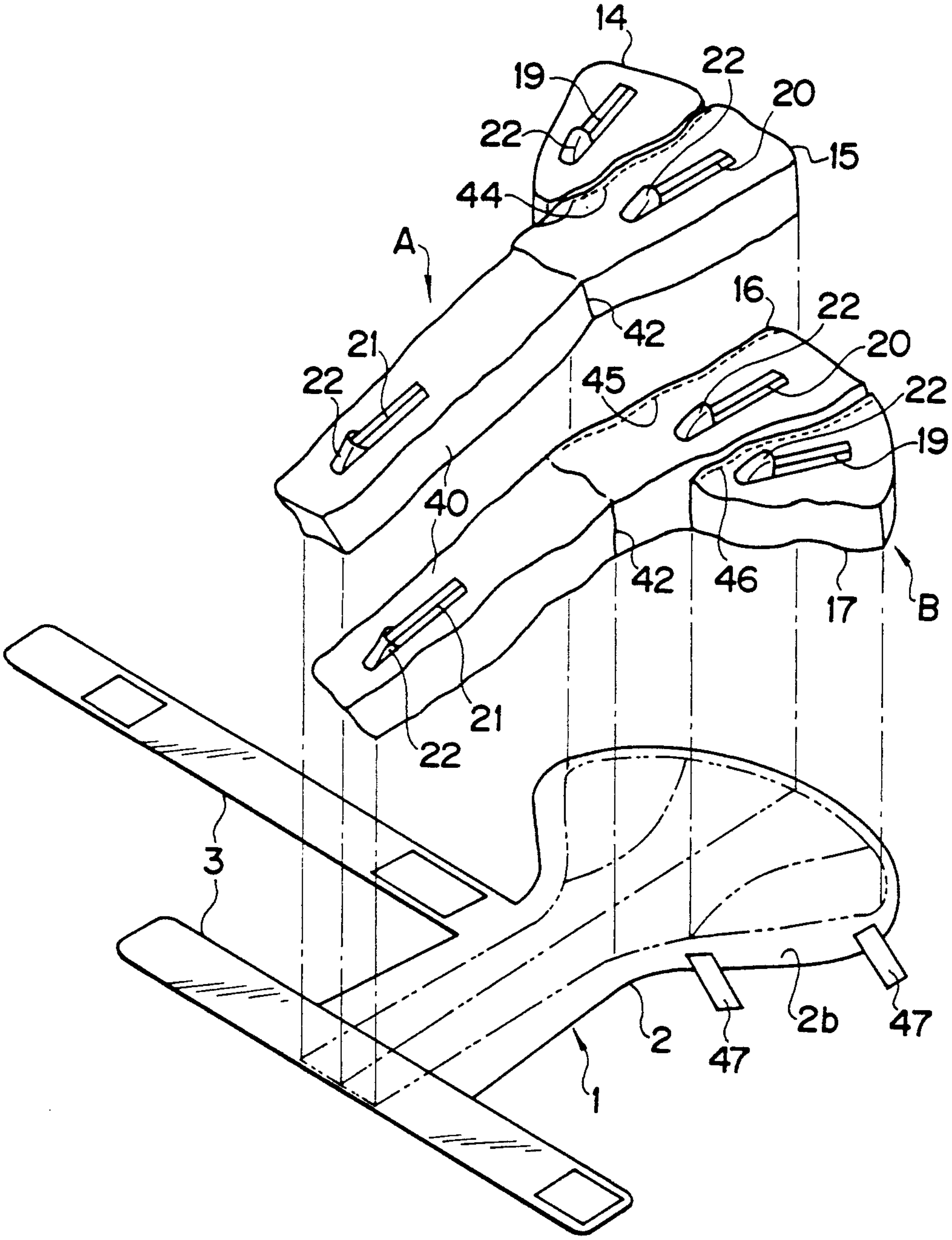
FIG. 6 is an exploded view of a portion of the device showing bag bodies in a state laid out to be sewn to a shaped foundation.

As shown in FIG. 2 and FIG. 6, the bag body A (B) comprises a (triangular) bag piece 14 (17) of a small length (height of the triangle) and a (rectangular) bag piece 15 (16) of a large length. The bag pieces 14 to 17 respectively accommodate air sacks 14*a*, 15*a*, 16*a* and 17*a* for allowing extension of finger joints. The trank 1 is provided with an arm stopper 3 for fastening the device to the wrist and forearm. Back hand straps 4, adapted to fasten the back of the hand to the device, are disposed at a location corresponding to the bases of the thumb and the index finger on the front side 2*a* of the glove foundation 2.

Eight air tubes 18 are connected one each to the air sacks 10*b* to 13*b* and 14*a* to 17*a*. These air tubes 18 are bundled with a tube band 47 and connected to a coupler 23 so as to be readily attached to and detached from a compressed air feed and discharge device (not shown).

Figure 5:
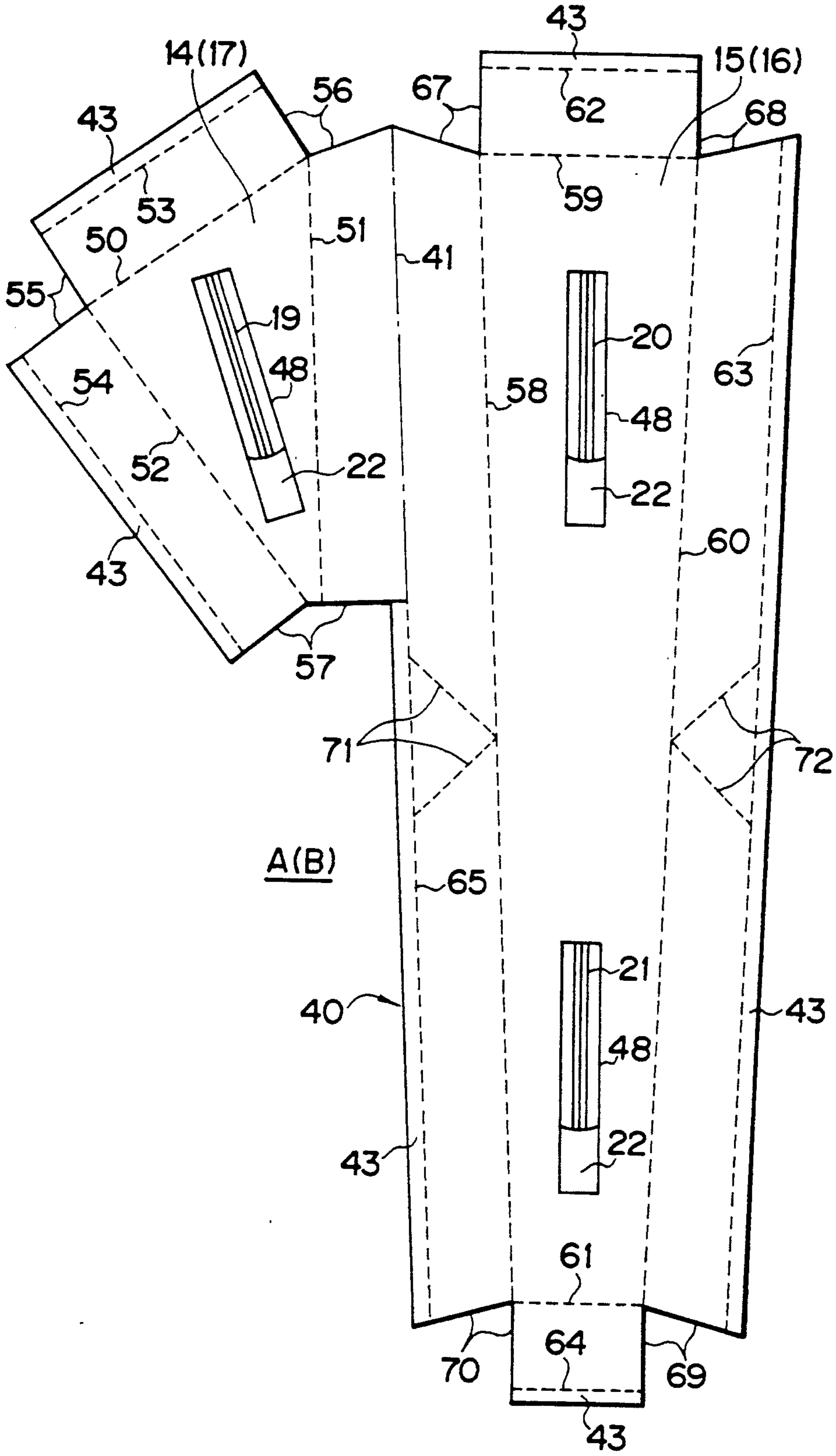
FIG. 5 is a plan view of a bag body of the device in an unassembled state.

The bag body A (B) is structured as shown in FIG. 5 and is formed as follows.

First, a foundation 40 of the prescribed shape of the bag body A is cut from cloth along the boundary of a pattern (not shown). Fastener windows 48 are provided in the foundation 40 for allowing the air sacks 14*a* (17*a*) and 15*a* (16*a*) to be placed in and taken out of the bag bodies. Slider covers 22 and slide fasteners 19 to 21 are jointly sewn to the foundation within the fastener windows 48.

Then, the bag piece 14 (17) of a small length is formed by folding the foundation about fold lines indicated by the dotted lines to form folds 50, 51, 52 and 53 and sewing together mutually adjoining parts 55, 56 and 57. The bag piece 15 (16) of a large length is formed as adjoined to the bag piece 14 (17) by folding the foundation first about a fold line indicated by the dot and chain line to form a fold 41 and about fold lines indicated by the dotted lines to form folds 58, 59, 60 and 61 and then by sewing together mutually adjoining parts 67, 68, 69 and 70.

A dart 42 is formed by sewing together parts 71 and 72 of the foundation located in the substantially central part of the bag piece 15 (16) of the large length. Thus, the bag body A (B) assumes a shape nearly resembling the letter V in an inverted spread form.

Since the bag bodies A and B are symmetrical, the bag body B is formed by inverting a shaped foundation 40 also cut from cloth and performing all of the steps mentioned above on this shaped foundation. Alternatively, the shaped foundation of the bag body B may be formed by using the pattern in its inverted form to cut the cloth.

The bag bodies A and B are sewn to the parts indicated with a two-dot chain line on the back side 2*b* of the glove foundation 2 with the bag pieces 15 and 16 adjoined to each other as illustrated in FIG. 6. Specifically, the foundation is folded about fold lines to form folds 53 and 54 and folds 62 to 65 to form flaps 43 which are folded back inside the bag bodies A and B. Then, these folds of the bag piece 14 (17) and the bag piece 15 (16) are sewn to the parts indicated by the two-dot chain line on the back side 2*b* of the glove foundation 2. Then, adjoining parts 44 to 46 of the bag pieces 14 to 17 are sewn together on the back side 2*b* of the glove foundation 2, thereby integrating the bag pieces 14 to 17 so that the trank 1 is prevented from being distorted when the compressed air is fed into the air sacks 14*a* to 17*a*.

Now, the operation of the present embodiment will be described below.

Figure 7:
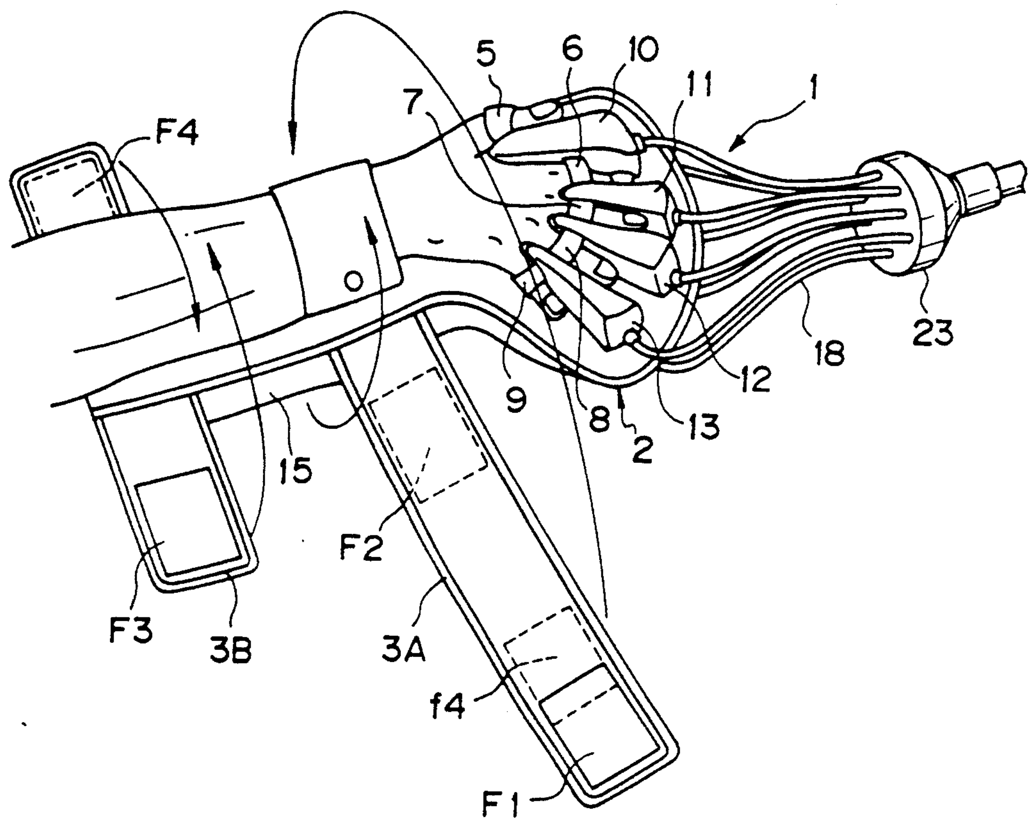
FIG. 7 is a perspective view of the device illustrating the emplacement of a pair of wrist straps and a hand arm strap on a hand.
Figure 8:
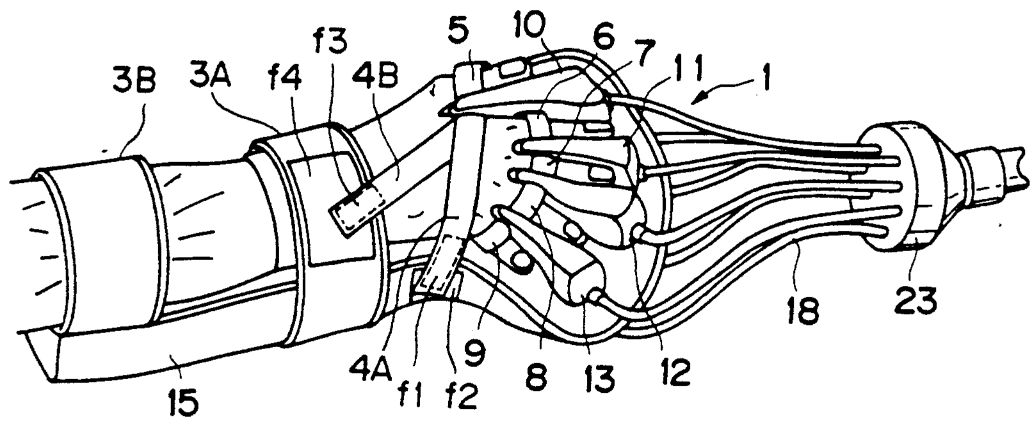
FIG. 8 is a perspective view of the device illustrating the emplacement of hand back straps on a hand.

When a palm is placed on the trank 1 as illustrated in FIG. 7, the thumb is fixed with the finger stopper 5, the index finger with the finger stopper 6, the middle finger with the finger stopper 7, the ring finger with the finger stopper 8, and the little finger with the finger stopper 9 respectively. The wrist and the forearm are infallibly fixed to the trank 1 by fastening hook and loop fasteners F1, F2, F3 and F4 of the type known by the trademark VELCRO provided on the arm straps 3A and 3B. Subsequently, the palm and the trank 1 are closely bound perfectly by fixing the back of the hand and the finger joints to the trank with two hand back straps 4A and 4B.

After the remedial device has been fitted to the hand as described above, the coupler 23 to which the air tubes 18 have been joined is connected to the compressed air feed and discharge device (not shown) and the compressed air is fed into the air sacks 10*b* to 13*b* and the air sacks 14*a* to 17*a*. The air sacks 10*b* to 13*b* for being inflated with the compressed air cause the fingers to be spread apart, and the air sacks 14*a* to 17*a* on being similarly inflated cause the finger joints and wrist joint to be extended and dorsiflexed.

By repeating the cycle of feeding the compressed air to the air sacks 10*b* to 13*b* and the air sacks 14*a* to 17*a* and, after an elapse of a required duration, discharging the compressed air from the air sacks, the device causes the hand joint in the state of dysfunction to undergo motions of extension and dorsiflexion and the fingers in a state of dysfunction to undergo a rhythmic and intermittent motion of being spread apart. As a result, the patient is relieved of troubles experienced in flexion, contracture and extension and, at the same time, the device gives rise in the patient to a factor for inducing autokinesis.

Figure 9:
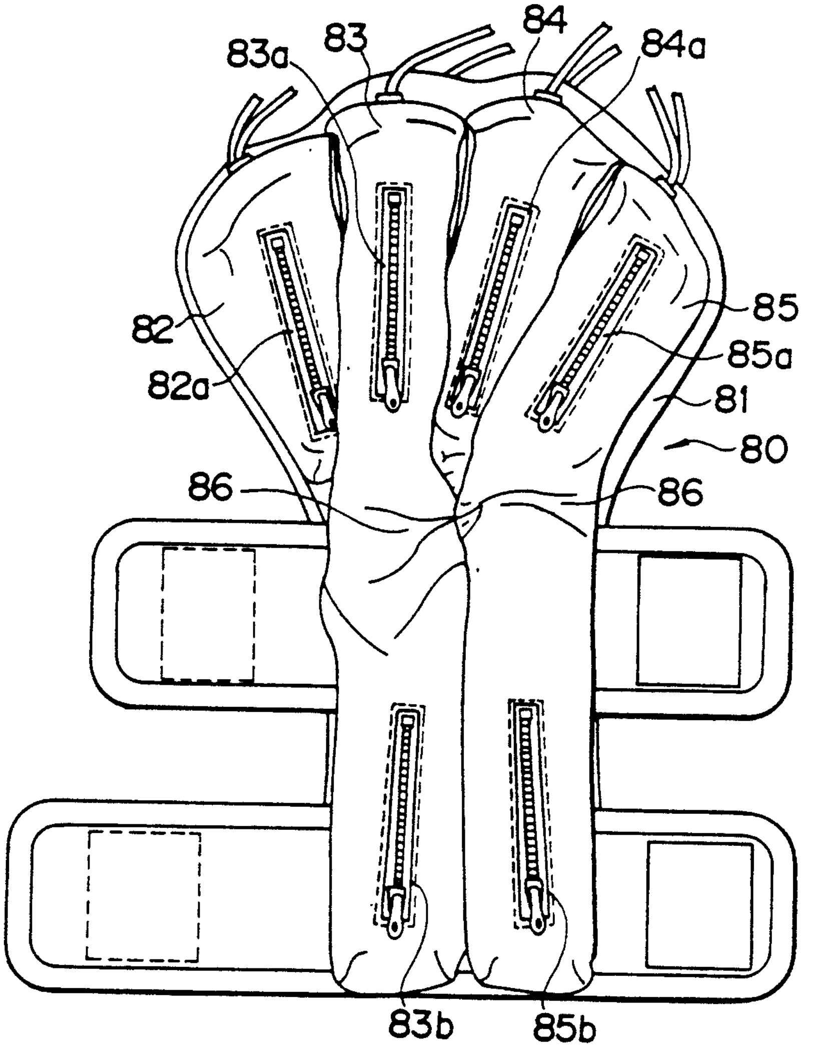
FIG. 9 PRIOR ART
FIG. 9 is a rear view of a conventional device.

In the present embodiment of the trank 1, the bag bodies A and B may well be thought of as substantially identical members because they are different only in that the shaped foundation 40 of either one of the bag bodies has been inverted to provide the other bag body or this other shaped foundation 40 has been cut from the pattern used to form the first bag body but then inverted. Therefore, the bag bodies A and B can be used just as well on the trank for the left hand (not shown) as on the trank for the right hand. To be specific, the bag body A can be used as a bag body A on the trank for the left hand and the bag body B as a bag body A on the trank for the left hand. In this device, the number of kinds of patterns for forming the bag bodies is 1 compared to 4 for the conventional device shown in FIG. 9 the number of kinds of bag bodies is 2 compared to 7 for the conventional device (the bag body 83 being usable for either of the tranks), and the time required for the manufacture of device from the time of cutting the cloth to that of sewing is about one third of the time required to manufacture the conventional device. Further, since the bag bodies are of a uniform kind and the discrepancies in the workmanship of sewing are entirely eliminated, the possibility that the trank 1 will be distorted because of a difference in twist and size between the bag bodies A and B or because of a difference in angle and position of dorsiflexion between the bag bodies A and B along their darts 4 is perfectly nil.

The slider covers 22 which are provided for the fasteners 10*a* to 13*a* and 19 to 21 of the trank 1 prevent the trank 1 from accidentally contacting the body of a patient during the therapy of the dysfunctional fingers and protect the patient against otherwise possible injury by the sliders of the fasteners. The tube straps 47 are capable of tying the eight air tubes 18 together into one bundle and consequently preventing the air tubes 18 from being intertwined or damaged.

As the arm stopper, a wrist strap 3A and a pair of forearm straps 3B are provided. The wrist strap 3A has the shape of a ribbon extended laterally from one side of the foundation 2 at the wrist and possesses a length large enough to be wound around the wrist at least one and a half times. The pair of forearm straps 3B are provided at a suitable distance from the wrist strap 3A. The two hand back straps 4A and 4*b* extend from the neighborhood of where the bases of the thumb and index finger are to lie on the front side of the foundation 2. Although the forearm straps 3B are to be used in the manner of a double door as conventionally practiced, the may be replaced by a straps of the same pattern as the wrist strap 3A for convenience sake. More than two back hand straps (4A and 4B) may be used when necessary.

The finger stoppers 5 to 9 are made of rubber and secured in place with VELCRO fasteners. The back hand straps 4A and 4B are similarly made of rubber and are provided on the back sides of their free ends with the loops f1 and f3 of the VELCRO fasteners. Hooks f2 of a VELCRO fastener are located near where the base of the little finger will lie on the back side of the foundation 2 and hooks f4 are located at the free end of the back side of the wrist strap 3A.

Loops F1 of the VELCRO fastener are disposed as securing means near the free end of the front side of the wrist strap 16, hooks F2 are located at the base of the back side of the wrist strap 3A, loops F3 of the VELCRO are located at the free end of the front side of the forearm strap 3B, and hooks F4 are located at the free end of the back side of the forearm strap 3B.

As described above, the present invention can produce the following outstanding effects.

Since this invention entails forming each bag body with a plurality of bag pieces and because such bag bodies can be used on tranks for either hand, the number of kinds of bag bodies needed is few and a small amount of time is required to manufacture the device ranging from the time of cutting foundations to form the bag bodies to the time of sewing the bag bodies together on the trank. Further, because this invention thoroughly eliminates the otherwise possible discrepancies in the workmanship in the sewing of the bag bodies owing to the standardization of the bag bodies, the condition of dorsiflexion provided by the tranks is totally uniform, the possibility of the trank being twisted or distorted upon the introduction of compressed air into the air sacks during use of the device for therapy is eliminated, and devices of uniform quality can be produced. Thus, this invention results in products of high economic utility which can be expected to offer a heretofore unattainable high curative effect.

Further, the infallibility with which the motion of expansion and the motion of extension and dorsiflexion are produced is enhanced because if the tightness by which the palm can be secured to the trank. Thus, the therapeutic effect of the remedial device is greatly enhanced.

What is claimed is:

1. A remedial device for the hand, said device comprising:

- a glove trank including a foundation having a front side on which the palm of a user of the device is to rest and a rear side, thumb and finger stops by which the thumb and fingers of a user of the device are secured to the foundation, and an arm stopper by which the wrist of a user of the device is secured to the foundation;
- a plurality of first bags disposed on the front side of said foundation;
- air sacks accommodated within said first bags;
- a pair of second bags disposed on the rear side of said foundation, each of said second bags comprising a one-piece foundation and having a concavity at which the one-piece foundation is folded about itself, a long rectangular portion located to one side of said concavity, and a triangular portion located to the other side of said concavity adjacent an end of the rectangular portion, the triangular portion having a height that is smaller than the length of the rectangular portion;

air sacks accommodated in the rectangular and the triangular portions of each of said second bags; and a compressed air feed line system by which compressed air can be fed into and discharged from said air sacks, the air sack accommodated within said first bags being located between where the fingers of a user will be secured to the foundation of the glove trank by the finger stoppers such that the fingers will be spread apart when air is fed into said air sacks accommodated within the first bags through said compressed air feed line system, and the air sacks accommodated within the second bags being so positioned on the rear side of the foundation of the glove trank as to cause joints of the hand of user of the device to be extended and dorsiflexed when air is fed into the air sacks accommodated within the second bags through said compressed air feed line system.

2. A remedial device for the hand as claimed in claim 1, wherein the rectangular portion of each of said second bags has a dart provided in a substantially central part thereof, said dart imparting a profile nearly resembling the letter V in an inverted spread form to the rectangular portion.

3. A remedial device for the hand, said device comprising:

a glove trank including a foundation having a front side on which the palm of a user of the device is to rest and a rear side, thumb and finger stops by which the thumb and fingers of a user of the device are secured to the foundation, and an arm stopper by which the wrist and forearm of a user of the device are secured to the foundation, said arm stopper including a wrist strap extending laterally from one side of the foundation of the glove trank and having a sufficient length to be wrapped around the wrist of a user at least one and a half times, fastening means for securing the free end of the wrist strap on the device while the wrist strap is wrapped at least one and a half times in the same direction around the wrist of a user of the device, and at least one forearm strap by which the forearm of a user can be secured to the foundation of the trank;

a plurality of first bags disposed on the front side of said foundation;

air sacks accommodated within said first bags;

a pair of second bags disposed on the rear side of said foundation; and air sacks accommodated within said second bags.

4. A remedial device for the had as claimed in claim 3, and further comprising a pair of hand back straps extending over a location where the back of the hand of a user of the device is to lie and intersecting one another at a location where the bases of the thumb and index finger of a user of the device are to lie.

5. A remedial device for the hand as claimed in claim 3, wherein said fastening means is a hook and loop fastener, and further comprising a hook and loop fastener associated with said at least one forearm strap.

6. A remedial device for the had as claimed in claim 4, wherein said fastening means is a hook and loop fastener, and further comprising a hook and loop fastener associated with said at least one forearm strap.

7. A remedial device for the hand as claimed in claim 3, wherein said at least one forearm strap comprises two straps extending laterally from the foundation of the trank.

8. A remedial device for the hand as claimed in claim 7, and further comprising a hook and loop fastener provided on the free ends of the two forearm straps.

9. A remedial device for the hand as claimed in claim 4, wherein said at least one forearm strap comprises two straps extending laterally from the foundation of the trank.

10. A remedial device for the hand as claimed in claim 9, and further comprising a hook and loop fastener provided on the free ends of the two forearm straps.

11. A remedial device for the hand as claimed in claim 3, wherein said wrist strap overlies said second bags when secured in position around the wrist of a user of the device by said fastening means.

* * * * *